United States Patent [19]

Nakanishi

[11] 4,202,102
[45] May 13, 1980

[54] DEVICE FOR OPENING AND CLOSING A CHUCK FOR A DENTAL HANDPIECE

[75] Inventor: Takasuke Nakanishi, Kanuma, Japan

[73] Assignee: Nakanishi Dental Mfg., Co., Ltd., Tochigi, Japan

[21] Appl. No.: 905,397

[22] Filed: May 12, 1978

[30] Foreign Application Priority Data

May 12, 1977 [JP] Japan .................................. 52-54932

[51] Int. Cl.$^2$ ............................................... A61C 9/00
[52] U.S. Cl. ....................................... 433/127; 279/51
[58] Field of Search .................. 279/51, 58; 32/26, 27

[56] References Cited

U.S. PATENT DOCUMENTS 1,741,734  12/1929  Pannwitz .............................. 279/51

Primary Examiner—Robert Peshock
Attorney, Agent, or Firm—Armstrong, Nikaido, Marmelstein & Kubovcik

[57] ABSTRACT

A device of this invention for opening and closing a chuck for a dental handpiece comprises a housing and an output shaft rotatably journalled in the housing. A cylindrical hollow is formed axially from a top end portion into the output shaft and a plurality of openings are formed at equally spaced portions around said shaft near an innermost portion of the hollow. A truncated cone-shaped column having a conical surface is firmly inserted into the innermost hollow of the output shaft to define a space for a small metallic driving ball. The small driving ball is rotatably inserted into each opening of said output shaft, and a large metallic driven ball is rotatably inserted into the hollow to abut against these small driving balls. A ball control sleeve having a tapering inner periphery is slidably fitted on the output shaft to locate at the openings. A cylindrical pusher including an axially cylindrical hollow is slidably inserted into the hollow of the shaft, then a chuck for a dental tool is slidably inserted to abut against said pusher. A rear control sleeve having a pair of inwardly diametrically extending pushing lugs and a cylindrical cavity formed around an inner periphery thereof is slidably fitted onto the output shaft. A helically convoluted expansion spring is inserted into the cylindrical cavity to surround the housing. A front control sleeve having the same pushing lugs as those of the rear control sleeve is slidably fitted onto the housing to insert into the cavity against the expansion spring, thus enabling the dentist to easily exchange the dental tool.

3 Claims, 4 Drawing Figures

DEVICE FOR OPENING AND CLOSING A CHUCK FOR A DENTAL HANDPIECE

BRIEF SUMMARY OF THE INVENTION

This invention relates to improvements in a chuck for a dental handpiece, and more particularly in a device for opening and closing a chuck for a dental handpiece which enables a dentist to easily exchange a dental tool.

According to a conventional dental handpiece, a cylindrical pusher for a chuck holding a dental tool is always pushed by a strong helical expansion spring so that when the tool is chucked, it is necessary to shift a slidable sleeve against the spring and also to maintain said sleeve as it is until the tool is inserted into the chuck. The expansion spring makes the device complicated and large, thus requiring troublesome operation for chucking or releasing the dental tool.

A principal object of this invention is to provide a device for closing and opening a chuck in a dental handpiece whereby dental tools such as drills, buffers, reamers, or the like can be easily and quickly chucked in or released out of the chuck.

Another object of this invention is to provide a device for closing and opening a chuck in a dental handpiece whereby the dental tools can be easily inserted into the normally open chuck and then be either held firmly or released therefrom by merely shifting a pair of a front and rear sleeves slidably fitted onto the dental handpiece.

A further object of this invention is to provide a device which will enable the dentist to exchange the dental tool within the dental handpiece for a new one in a simpler and faster method and with ease of operation.

A still another object of this invention is to provide a device suitable for the aforementioned purposes which will be comparatively simple and small in construction and at the same time desirably rigid, strong and durable.

BRIEF DESCRIPTION OF DRAWINGS

While I have shown in the accompanying drawings, a preferred embodiment of my invention, it should be understood that the same is susceptible of modification and change without departing from the spirit of my invention.

Referring to the drawings.

DETAILED DESCRIPTION

Figure 1:
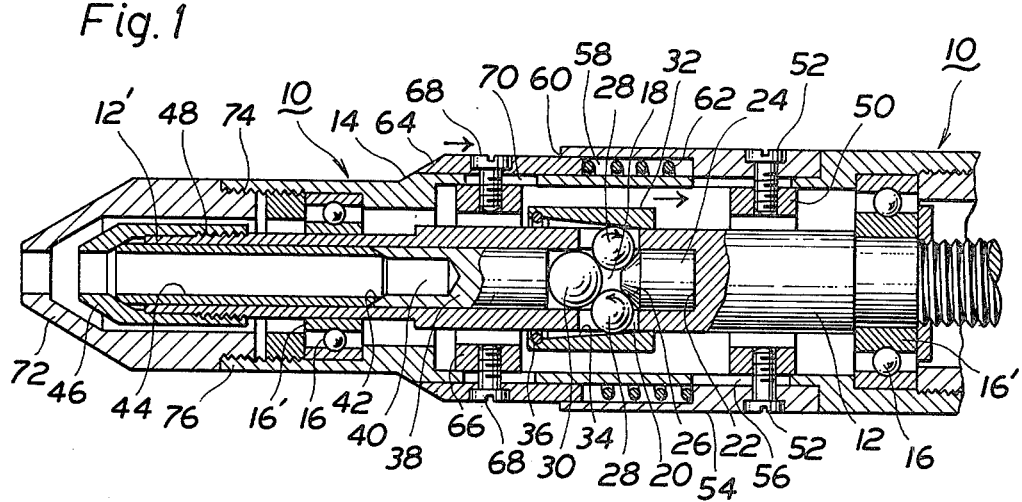
FIG. 1 is a fragmentary enlarged vertical sectional view of an embodiment of a dental handpiece comprising a device of this invention, with a chuck opened.
Figure 2:
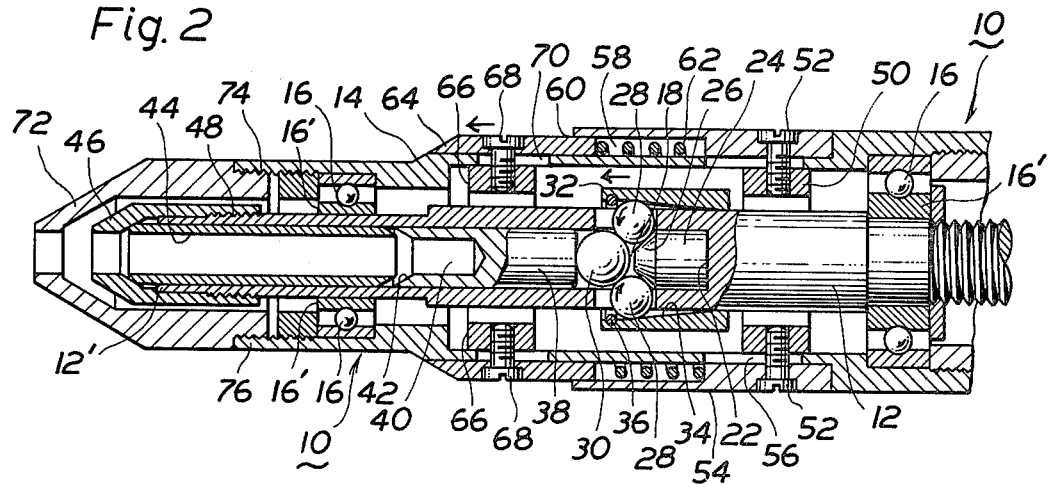
FIG. 2 is a similar enlarged vertical sectional view of the dental handpiece, showing the closed chuck.
Figure 3:
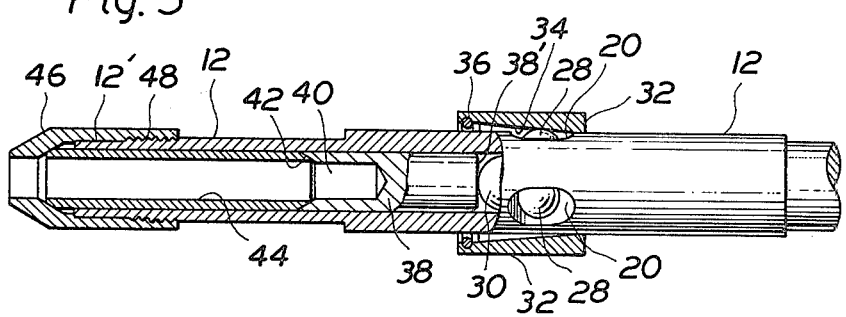
FIG. 3 is a fragmentary side elevation of an output shaft, partly in section.

Referring to FIGS. 1, 2 and 3, a preferred embodiment which has been selected to illustrate this invention comprises a dental handpiece, in which an output shaft 12 is journaled for rotation in a housing 10 having a conically tapering end portion 14 by means of antifriction bearings 16 and 18.

There is mounted on the output shaft 12 an inner race 16', 16' for the ball bearing 16, 16 of the epicyclic or planetary ball gear, said inner races being so connected with the output shaft 12 that it rotates with the inner races.

A cylindrical hollow 18 is formed axially from a top end portion 12' into the output shaft 12, and also a plurality of openings 20 are formed at equally spaced portions around the output shaft 12 near an innermost portion 22 of the hollow 18.

A truncated cone-shaped column 24 having a diameter to fit to that of the hollow 18, a length extending from the innermost portion 22 and stretching slightly into a portion corresponding to the openings 20 and a conical surface 26 is firmly inserted into the innermost hollow 18 of the output shaft 12, thus defining a space for a small metallic driving ball 28, which is rotatably inserted into each opening 20 of the output shaft 12, and a metallic driven ball 30 larger than the ball 28 is rotatably inserted into the hollow 18 to abut against the balls 28 so that a semisphere of the ball 28 is partially protruded through and beyond the opening 20.

A ball pushing sleeve 32 having a forward outwardly tapering inner periphery 34 and an O-ring 36 around said periphery adjacent to an outer orifice thereof is slidably fitted onto the output shaft 12 to locate at the openings 20 thereof, thus preventing said ball pushing sleeve from disengaging out of the output shaft 12. Accordingly, each small driving ball 28 abuts against the inner periphery 34, the conical surface 16 and the large driven ball 30.

A cylindrical pusher 38 including an axially cylindrical hollow 40 from a conically tapering orifice 42 is slidably inserted into the hollow 18 to abut against the large metallic ball 30.

Into the hollow 18 is slidably inserted a chuck 44, and a cap 46 is threadedly mounted onto a screw thread 54 around the top end portion 12' of the output shaft 12.

A rear control sleeve 54 having a pair of inwardly diametrically extending pushing lugs 50 held by a bolt 52 extending through a wall of said sleeve and a cylindrical cavity 58 formed around an inner periphery contiguous to an orifice 60 thereof is slidably fitted onto the housing 10 to locate around the openings of the output shaft 12 so that the ball pushing sleeve 32 may be displaced axially by these pushing lugs 50. A helically convoluted expansion spring 62 is inserted into the cavity 58 to surround the housing 10, and it is adapted to abut with one end against an innermost portion of the cavity 58, urging the ball pushing sleeve 32 towards a subsequently mentioned front control sleeve 64 which is also fitted onto the housing 10.

A pair of inwardly diametrically extending pushing lugs 66 are provided by bolts 68 extending through a wall thereof and elongated grooves 70 in such a manner that the pushing lugs 66 may be displaced axially in accordance with an axial movement of the front control sleeve 64. The diameter of the front control sleeve 64 is slightly shorter than that of the rear control sleeve 54 so that said front control sleeve may be slidably inserted into the cavity 58 of the rear control sleeve 54 to push the expansion spring 62 rearwardly.

A cap 72 is threadedly mounted into a screw thread 74 around a top end portion 76 of the housing 10.

Figure 4:
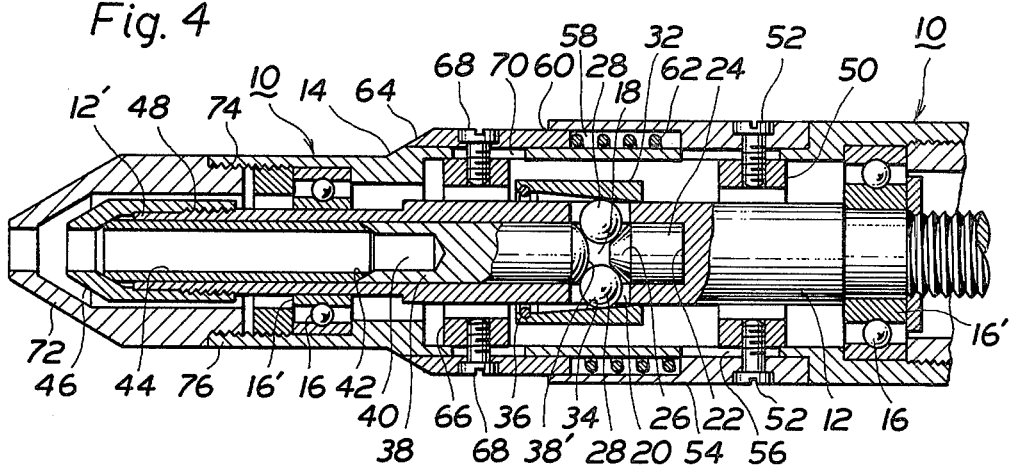
FIG. 4 is a fragmentary vertical sectional view of another embodiment of a device of this invention.

It should be noted in the embodiment shown in FIG. 4 that a rear end portion of the cylindrical pusher 38 for the chuck 44 is shaped into a semispherical face 38' so that the large metallic driven ball 30 used in the embodiments in FIGS. 1, 2 and 3 may be omitted, thus directly abutting against a plurality of the small metallic driving balls 28.

When a dental tool is inserted into the dental handpiece by closing the chuck 44, the rear control sleeve 54 shown in FIG. 2 is slidably displaced forwardly by fingers, and the pushing lugs 50 integral with said rear control sleeve is moved forwardly to push a rear side orifice of the ball pushing sleeve 32. At the same time, the small driving balls 28, which are partially protruding out of the openings 20, are forced to roll as depicted by an arrow in each ball along the forward outwardly tapering inner periphery 34 of the ball pushing sleeve 32 in accordance with the forward movement thereof, thus rolling these small balls deep into the openings 20 and forwardly along the conical surface 26 of the truncated column 24. At this position, the rolling pressure of these small driving balls 28 abutting against the large ball 30 are transmitted to the latter, which in turn is driven to displace the pusher 38 axially forwardly and also to close the chuck 44 as depicted in FIG. 1.

When the fingers in contact with the rear control sleeve 54 are released, said rear control sleeve returns axially backward to the original position by means of the expansion spring 62, and the ball pushing sleeve 32 is kept as shown in FIG. 1, for no reaction is given to said sleeve.

In order to open the chuck 44, the front control sleeve 64 as shown in FIG. 1 is slidably displaced by fingers backward to push a front side orifice of the ball pushing sleeve 32 by the pushing lugs 66 and also to roll the small balls 28 as shown by an arrow in each ball, thus releasing these small balls under pressure to protrude partially out of the openings 20 of the output shaft 12. Accordingly, the pusher 38 for the chuck 44 is driven to return to the original position shown in FIG. 2 to open said chuck.

In the embodiment shown in FIG. 4, the large driven ball 30 is not used so that the rolling pressure of the small driving balls are directly transmitted to the rear semispherical face 38'. Other function and movement are carried out the same as those of the embodiments shown in FIGS. 1-3.

According to the ordinary handpiece comprising a helically convoluted strong expansion spring adapted to push the chuck pusher itself, it has been necessary to displace the slidable control sleeve against the strong expansion spring for chucking the dental tool and also to maintain the sleeve as it is until the dental tool has been actually inserted.

On the contrary, it is quite easy for the dentist with the device of this invention to insert the dental tool into the normally opened chuck 44 and also to shift axially slidably the front and rear control sleeves 64 and 54, which are made to work against the helically convoluted weak expansion spring 62 to open and close the chuck 44.

In addition, the ball pushing sleeve 32 can be displaced axially smoothly through the rolling friction caused between the small dirving balls 28 and the forward outwardly tapering inner periphery 34 of said sleeve so that the mutual power transmission among the small driving balls 28, the large driven ball 30 and the semispherical face 38' of the chuck pusher 38 may be carried out effectively to open and close the chuck 44 quickly.

I claim:

1. A device for opening and closing a chuck for a dental handpiece comprising: a housing having a conically tapering end portion; an output shaft journalled for rotation in said housing, said output shaft having a hollow axial portion therein and a plurality of openings formed at equally spaced portions around said output shaft; a truncated cone-shaped column positioned in the innermost end of said hollow portion, said column having a diameter equal to that of said hollow portion, and a length extending from the innermost end of said hollow portion to said openings in said output shaft; a plurality of driving balls, each rotatably positioned in one of said openings in said output shaft; a driven ball rotatably positioned in said hollow portion of said output shaft to abut against said driving balls such that a portion of each of said driving balls protrudes from its corresponding opening; a ball pushing sleeve mounted for axial displacement on said output shaft, said sleeve having an outwardly tapering inner periphery and a means around said periphery adjacent to an outer orifice thereof to prevent disengagement from said output shaft, said tapering inner periphery contacting said driving balls; a cylindrical pusher slidably positioned in said hollow portion of said output shaft to abut against said driven ball, said pusher including a cylindrical hollow and also a tapering orifice; a chuck mounted in said hollow portion of said output shaft for displacement axially within said hollow portion and abutting against said cylindrical pusher; a cap mounted around the outermost end of said output shaft; a rear control sleeve means mounted on said housing for axial displacement thereon, said rear sleeve means including first lugs positioned within said housing for contacting one end of said ball pushing sleeve upon the displacement of said rear control sleeve means in a first direction; a front control sleeve means mounted on said housing for axial displacement thereon, said front control sleeve means including second lugs positioned within said housing for contacting the other end of said ball pushing sleeve upon displacement of said front control sleeve means in a second direction opposite to said first direction; and spring means positioned between said rear and front control sleeve means for biasing said rear control sleeve means in said second direction and for biasing said front control sleeve means in said first direction; wherein the movement of said front and rear control sleeve means causes said first and second lugs to engage corresponding ends of said pushing sleeve and thereby move said pushing sleeve in said first and second directions, thereby moving said driven balls into and out of said holes in said output shaft whereby said driven ball is moved axially in said hollow portion of said output shaft, thereby opening and closing said chuck.

2. A device for opening and closing a chuck for a dental handpiece comprising: a housing having a conically tapering end portion; an output shaft journalled for rotation in said housing, said output shaft having a hollow axial portion therein and a plurality of openings formed at equally spaced portions around said output shaft; a truncated cone-shaped column positioned in the innermost end of said hollow portion, said column having a diameter equal to that of said hollow portion, and a length extending from the innermost end of said hollow portion to said openings in said output shaft; a plurality of driving balls, each rotatably positioned in one of said openings in said output shaft; a cylindrical pusher means slidably positioned in said hollow portion of said output shaft, one end of said cylindrical pusher having a semi-spherical shape which abuts against said driving balls such that a portion of each of said driving balls protrudes from its corresponding opening, said pusher including a cylindrical hollow and also a tapering orifice; a ball pushing sleeve mounted for axial displacement on said output shaft, said sleeve having an outwardly tapering inner periphery and a means around said periphery adjacent to an outer orifice thereof to prevent disengagement from said output shaft, said tapering inner periphery contacting said driving balls; a chuck mounted in said hollow portion of said output shaft for displacement axially within said hollow portion and abutting against said cylindrical pusher, a cap mounted around the outermost end of said output shaft; a rear control sleeve means mounted on said housing for axial displacement thereon, said rear sleeve means including first lugs positioned within said housing for contacting one end of said ball pushing sleeve upon the displacement of said rear control sleeve means in a first direction; a front control sleeve means mounted on said housing for axial displacement thereon, said front control sleeve means including second lugs positioned within said housing for contacting the other end of said ball pushing sleeve upon displacement of said front control sleeve means in a second direction opposite to said first direction; and spring means positioned between said rear and front control sleeve means for biasing said rear control sleeve means in said second direction and for biasing said rear control sleeve means in said second direction and for biasing said front control sleeve means in said first direction, wherein the movement of said front and rear control sleeve means causes said first and second lugs to engage corresponding ends of said pushing sleeve and thereby move said pushing sleeve in said first and second directions, thereby moving said driving balls into and out of said holes in said output shaft whereby said cylindrical pusher means is moved axially in said hollow portion of said output shaft, thereby opening and closing said chuck.

3. A device as set forth in claims 1 or 2 wherein said rear control sleeve means has a larger outer diameter than the outer diameter of said front control sleeve means and said rear control sleeve means has a hollow inner portion having a diameter larger than the outer diameter of said front control sleeve means and wherein said spring means is positioned in said hollow portion in said rear control sleeve means and a portion of said front control sleeve means is positioned in said hollow portion of said rear control sleeve means for holding said spring means therein.

* * * * *